United States Patent [19]
Takahashi et al.

[11] Patent Number: 5,902,907
[45] Date of Patent: May 11, 1999

[54] METHOD FOR PRODUCTION OF FLUORENONE

[75] Inventors: Tsukasa Takahashi; Yasuhisa Emoto, both of Hyogo, Japan

[73] Assignee: Nippon Shokubai Co., Ltd., Osaka-fu, Japan

[21] Appl. No.: 08/968,227

[22] Filed: Nov. 12, 1997

Related U.S. Application Data

[63] Continuation-in-part of application No. 08/759,193, Dec. 5, 1996, abandoned.

[30] Foreign Application Priority Data

Dec. 11, 1995 [JP] Japan ................................ 7-321370
Dec. 11, 1995 [JP] Japan ................................ 7-321371

[51] Int. Cl.$^6$ ................................................ C07C 45/02
[52] U.S. Cl. ................................................ 568/321
[58] Field of Search ................................ 568/321

[56] References Cited

U.S. PATENT DOCUMENTS

| | | | |
|---|---|---|---|
| 3,875,237 | 4/1975 | Niznik | 568/321 |
| 4,218,400 | 8/1980 | Finger | 568/321 |
| 4,297,514 | 10/1981 | Ma | 568/321 |
| 5,545,760 | 8/1996 | Walters et al. | 568/321 |

FOREIGN PATENT DOCUMENTS 60-233028  11/1985  Japan ................................ 568/321

*Primary Examiner*—James H. Reamer
*Attorney, Agent, or Firm*—Omri M. Behr, Esq.

[57] ABSTRACT

A method for the production of fluorenone for the vapor-phase catalytic oxidation of fluorene with a molecular oxygen-containing gas, which including adjusting the molar ratio of fluorene to molecular oxygen in a feed raw material gas composed of fluorene as a raw material and a molecular oxygen-containing gas in the range of 1:1 to 0.13:1, or keeping the sulfur content in a raw material fluorene at or below 0.15% by weight.

14 Claims, 1 Drawing Sheet

FIGURE
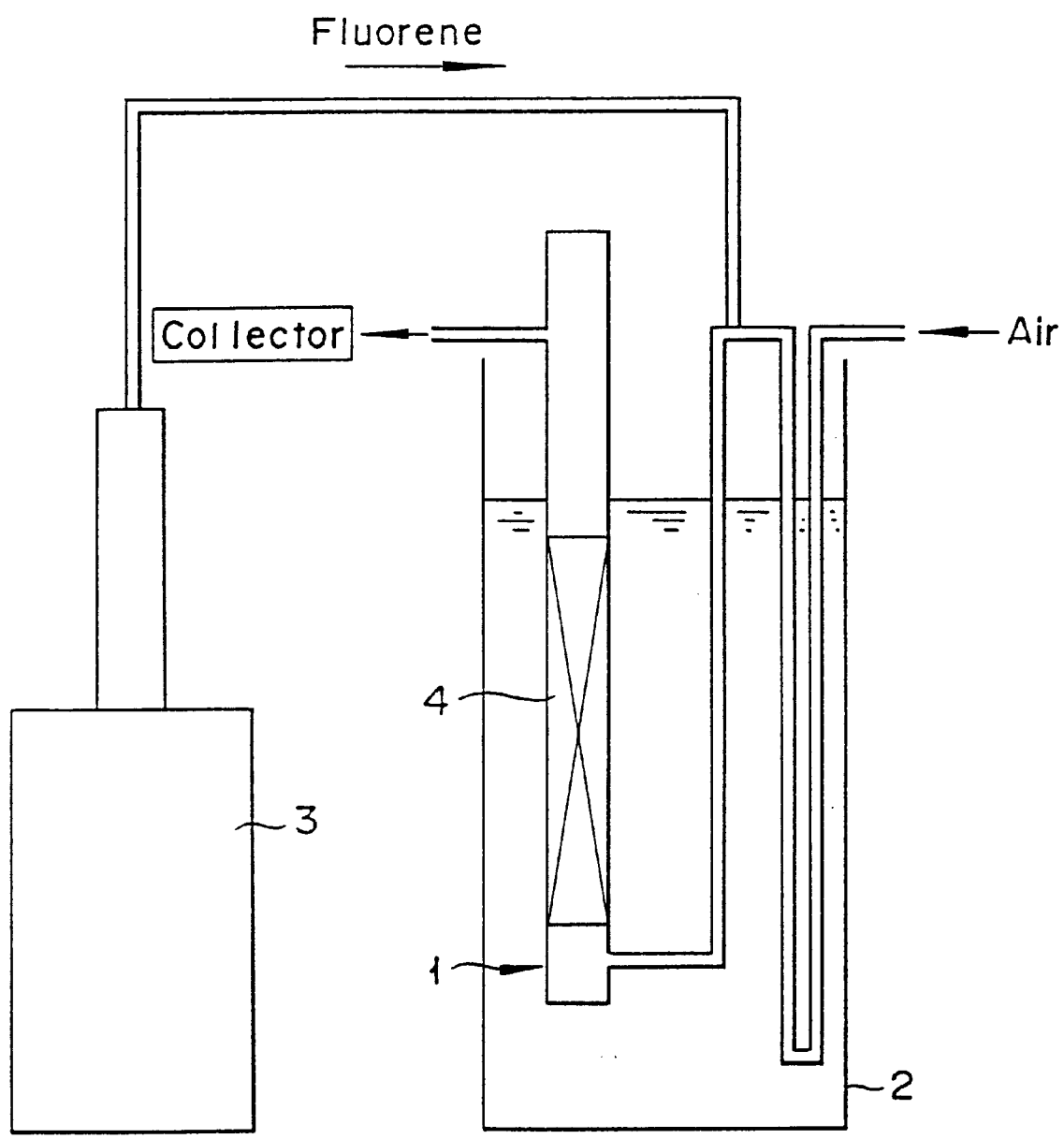

METHOD FOR PRODUCTION OF FLUORENONE

This application is a continuation-in-part of application Ser. No. 08/759,193, filed Dec. 5, 1996, now abandoned.

BACKGROUND OF THE INVENTION

1. Field of the Invention

This invention relates to a method for the production of fluorenone and more particularly to a method for producing fluorenone by the vapor-phase catalytic oxidation of fluorene with a high yield. Fluorenone is a commercially useful substance as raw materials for agricultural pesticides, medicines, and functional macromolecular compounds.

2. Description of the Related Art

The method for producing fluorenone by the vapor-phase catalytic oxidation of fluorene with molecular oxygen is at an advantage in enjoying high productivity as compared with the liquid-phase method and avoiding emission of waste liquor. It is nevertheless at a disadvantage in having to sacrifice selectivity when the reaction is performed at a high conversion. It incurs difficulty in effectively utilizing fluorene while maintaining high productivity. It does not easily produce fluorenone stably with high yield because it entails the phenomenon of suffering the selectivity of fluorenone to be lowered and the catalytic activity to be varied, depending on the quality of the raw material fluorene to be used.

The method for the production of fluorenone is known in two types, the liquid-phase method and the vapor-phase method. As to the liquid-phase method, many reports have been published on the method of liquid-phase oxidation with molecular oxygen by the use of a phase-transfer catalyst formed of an aqueous alkali solution, a hydrophobic organic solvent, and a quaternary ammonium salt (JP-A-07-82,206 and JP-A-07-82,207). As to the vapor-phase method, a method using vanadium pentoxide (U.S. Pat. No. 1,374,695), a method using a catalyst formed of iron vanadate and potassium sulfate (Zh. Pyirl Khim 35, 693–696 (1962)), a method using a catalyst formed of vanadium pentoxide and tin oxide (Engineering Chemical Journal, 56, (6), 413–416 (1953)), a method for causing inclusion of a large volume of water by the use of a catalyst formed of at least one metal element of the fifth and sixth groups of the periodic system (U.S. Pat. No. 1,892,768), a method using a catalyst formed of vanadium pentoxide, silica, and potassium sulfate (U.S. Pat. No. 2,956,065), and a method using a catalyst formed of a vanadium oxide, titania, and an alkali metal compound (JP-A-60-233,028) have been disclosed. In addition to these methods, a method using a catalyst formed of a system of vanadium-iron-cesium (Stud, Surf, Sci. Catal. (1993), 75 (New Frontiers in Catalysis, Pt. A), 707–17) has been also disclosed.

It has been heretofore known that a vanadium-based catalyst can be used as an effective catalyst for the production of fluorenone by the vapor-phase oxidation of fluorene. It has been difficult, however, to obtain fluorenone stably with a high yield because the reaction performed at a high conversion results in lowering the selectivity and the quality of the raw material lowers the selectivity or changes the catalytic activity.

An object of this invention, therefore, is to provide an improved method for the production of fluorenone.

Another object of this invention is to solve the problems heretofore attendant on the vapor-phase oxidation and provide a method for producing fluorenone stably with high selectivity.

SUMMARY OF THE INVENTION

The objects mentioned above are accomplished, in the production of fluorenone by the vapor-phase catalytic oxidation of fluorene with a molecular oxygen-containing gas, by a method for the production of fluorenone which comprises adjusting the molar ratio of fluorene to molecular oxygen in a feed raw material gas containing fluorene as a raw material and a molecular oxygen-containing gas in the range of 1:1 to 0.13:1 and the fluorene contents per 1 $Nm^3$ of the feed raw material gas being in the range of not less than 200 $g/Nm^3$; and subjecting the oxidation of fluorene in the presence of a catalyst formed of at least one metal element of the fifth and sixth groups of the peridic table. This range, when air is used as the molecular oxygen-containing gas, corresponds approximately to a fluorene content in the range of 200 to 1280 g per 1 $Nm^3$ of the feed raw material gas.

The objects are further accomplished, in the production of fluorenone by the vapor-phase catalytic oxidation of fluorene with a molecular oxygen-containing gas, by a method for the production of fluorenone which comprises preparing the raw material fluorene having a sulfur content at or below 0.15% by weight; adjusting the molar ratio of fluorene to molecular oxygen; and subjecting the oxidation in the presence of a catalyst formed of at least one metal element of the fifth and sixth groups of the periodic table.

Our study has evolved a knowledge that in the vapor-phase catalytic oxidation of fluorene with a molecular oxygen-containing gas, the fluorenone is obtained at a high conversion with high selectivity by adjusting the fluorene concentration in the feed raw material gas comprising fluorene as a raw material and the molecular oxygen-containing gas within a range higher than that of a conventional method. This invention has been perfected as a result of this knowledge. We have tested various species of fluorene as the raw material and studied about the conditions for stably producing fluorenone by the vapor-phase catalytic oxidation, to find that the sulfur component in the raw material fluorene affects the catalytic activity and the selectivity of fluorenone. We have perfected this invention based on this knowledge.

According to this invention, fluorenone can be produced at a high conversion with high selectivity by the vapor-phase catalytic oxidation of fluorene. Particularly, this invention accomplishes the high selectivity with the conversion of fluorene kept at such a high level as that approximating closely to 100%.

BRIEF DESCRIPTION OF THE DRAWINGS

FIGURE is a schematic diagram of a reaction apparatus to be used in examples and comparative examples herein.

DESCRIPTION OF THE PREFERRED EMBODIMENT

The fluorene to be used as the raw material in this invention may be any of various species of fluorene such as, for example, the fluorene which is obtained from a fluorene-containing oil derived from coal tar (tar type fluorene) and the fluorene which is obtained from the residual oil by-produced in the process for the production of dealkylated benzene (petroleum process type fluorene). The raw material fluorene does not need to completely consist of fluorene but may contain various impurities arising from the starting raw material or the process of purification such as, for example, biphenyl compounds like methyl biphenyl, naphthalene compounds like methyl naphthalene, fluorene derivatives like 9-methyl fluorene, and dibenzofuran.

Even when the fluorene concentration in the raw material fluorene is not more than 60% by weight, the production of fluorenone may be obtained with a high yield. In consideration of the necessity for a subsequent step for purification, however, it is appropriate to use the raw material fluorene having a fluorene concentration of not less than 70% by weight, preferably not less than 80% by weight.

The catalyst to be used for the vapor-phase catalytic reaction according to this invention is not particularly limited. Any of the catalysts that are generally used for the vapor-phase oxidation of fluorene into fluorenone can be used. A concrete example of the catalyst which is effectively usable herein, includes a catalyst formed of at least one metal element of the fifth and sixth groups of the periodic table, such as, vanadium, molybdenum and tungsten, and optionally of an alkali metal, tin, silicon and titanium. Among them, a catalyst formed of titanium, vanadium and cesium as the construction elements is used particularly advantageously. Here, the atomic ratio of alkali metal element to vanadium preferably falls in the range of 0.8:1 to 8:1, preferably 1:1 to 5:1, particularly preferably 1:1 to 3:1. It is particularly advantageous to use a supported catalyst having such a catalytically active component as mentioned above deposited on an inert carrier such as silicon carbide, alumina, silica, silica-alumina, or pumice. Incidentally, the carried catalyst is in the form of spheres, cylinders, saddles, or cylindrical particles which generally have a particle diameter in the range of 3 to 15 mm, preferably 3 to 10 mm.

One of the characteristics of this invention, in the oxidation to be effected by causing a feed raw material gas comprising fluorene and a molecular oxygen-containing gas to contact with the catalyst mentioned above, resides in adjusting the molar ratio of fluorene to molecular oxygen in the feed raw material gas in the range of 1:1 to 0.13:1, preferably 0.9:1 to 0.3:1, and most preferably 0.8:1 to 0.6:1. If the molar ratio of the fluorene to molecular oxygen in the feed raw material gas is more than 1:1, oxygen becomes insufficient and the conversion of fluorene is lowered rapidly. The above-mentioned molar ratios, when air is used as the molecular oxygen-containing gas, correspond to the fluorene contents in the range of 200 to 1280 g/Nm$^3$, 450 to 1170 g/Nm$^3$, and 900 to 1060 g/Nm$^3$, per 1 Nm$^3$ of the feed raw material gas, respectively.

It is significantly meaningful to increase the concentration of raw material gas in vapor-phase catalytic reactions in view of improvement in productivity, but at the same time very difficult to do so. This is because in such a case larger amounts of heat generate to heighten the temperature of the hot spot in the catalyst layer used, and thus the generation rate of the combustion gas is to be increased. Also, it sometimes occurs that the conversion thereof decreases since the catalyst does not convert all of the raw material gas fed, and intermediate products and by-products are increased, so that the yield thereof decreases. In contrast, by heightening the raw material gas concentration in a case of vapor-phase catalytic oxidation of fluorene to fluorenone, the inventors have found that the selectivity can be increased while approximately 100% of the conversion is kept, and thus the present invention has been developed. In addition, it is also a surprising fact that the oxidation can be carried out in a high concentration of a raw material gas, e.g., not less than 200 g/Nm$^3$, which concentration is extremely high in the field of vapor-phase oxidation, and as a result the yield is conversely increased.

In the context of this invention, the term "molar ratio of fluorene to molecular oxygen" is defined as a molar ratio of (moles of pure fluorene)/{(moles of molecular oxygen in the raw material gas)-(moles of oxygen to be consumed by impurities)}. Examples of the molecular oxygen-containing gas include normally air, as well as oxygen-rich air, and a mixed gas of air with an inert gas such as nitrogen and carbon dioxide. Further, the raw material gas, when necessary, may be used as diluted with steam.

Even when pure oxygen is used as the molecular oxygen-containing gas in the method of this invention, the fluorene concentration in the feed raw material gas does not exceed 3710 g/Nm$^3$ because of the requirement that the molar ratio of fluorene to molecular oxygen should be in the range of 1:1 to 0.13:1. It is thought appropriate to use normally air as a molecular oxygen-containing gas from the economic point of view. In this case, the fluorene concentration in the feed raw material gas does not exceed 1280 g/Nm$^3$.

Another characteristic of this invention resides in keeping the sulfur concentration in the raw material fluorene at or below 0.15% by weight, preferably at or below 0.1% by weight, and more preferably at or below 0.05% by weight, based on the weight of the raw material fluorene. If the sulfur concentration in the raw material fluorene exceeds 0.15% by weight and reaches 0.2% by weight, for example, the production of fluorenone will not be attained with high yield (refer to below Controls). The reason for this critical sulfur concentration remains yet to be elucidated. It may be logically explained, however, by a supposition that the sulfur heightens the activity of the oxidizing catalyst used in the reaction and abnormally promotes the oxidizing reaction or the combustion reaction. When the raw material fluorene having a sulfur concentration of 0.2% by weight is used for the oxidizing reaction, for example, the temperature of the hot spots in the catalyst bed rises to encourage the combustion reaction and notably lower the selectivity of fluorenone. When the sulfur concentration in the raw material fluorene is decreased substantially to 0, the rise of the temperature of the hot spots can be effectively repressed and the reaction can be stably continued.

The term "sulfur concentrations" as used in this invention refers to the concentration as sulfur of the total amount of organic and inorganic sulfur compounds present in the raw material fluorene, as determined by "the method for testing sulfur content of petroleum product by means of combustion tube" specified in JIS (Japanese Industrial Standard) K-2547.

The sulfur concentration in the raw material fluorene can be adjusted at or below 0.15% by weight by purification due to distillation or crystallization or by various methods used for the desulfurization of petroleum. The method to be used for this purpose is not particularly limited. It is particularly proper that the sulfur concentration should be not more than 0.05% by weight.

The reaction conditions such as the temperature, the spatial velocity, and the like -to be involved in the vapor-phase catalytic oxidation contemplated by this invention are not limited particularly but may be suitably selected, depending on the kind of the catalyst to be used, for example.

Generally, the reaction temperature is selected in the range of 250° to 480° C., preferably 300° to 450° C. and the spatial velocity in the range of 100 to 10,000/hr, preferably 200 to 5,000/hr.

Now, this invention will be described more specifically below with reference to Production Example, examples and comparative examples.

Preparation Example 1

A homogenous solution was obtained by stirring 13.4 g of ammonium vanadate, 26.8 g of oxalic acid, 2.4 g of potassium sulfate, and 25.1 g of cesium sulfate in 180 ml of purewater at 80° C. This solution was cooled to room temperature. A homogeneous slurry was formed by thoroughly stirring 120 g of anatase type titanium dioxide having a surface area of 20 m$^2$/g and 4.8 g of silicon carbide whiskers in the cooled solution. A slurry for the preparation of catalyst was obtained by adding 400 ml of pure water to the resultant slurry.

A stainless steel heatable rotary drum was charged with 200 g of beads of silicon carbide carrier of 4 mm in average diameter, and set rotating. The silicon carbide carrier in the rotating kiln was kept at a temperature in the range of 180° to 220° C. and 20 g of the slurry for the preparation of catalyst mentioned above was sprayed and deposited on the beads of silicon carbide carrier. The beads now having the catalyst carried thereon were calcined as swept with a stream of air at 550° C. for five hours, to prepare an oxidizing catalyst. The atomic ratio of each added element was as follows. V:Cs:K:S:TiO$_2$=7.64:9.26:1.84:5.55:100

Comparative Example 1

In a stainless steel reaction tube 1 of 20 mm in inside diameter, the oxidizing catalyst which was obtained in the above Preparation Example 1 was packed in a bed length of 180 mm on the gas outlet side of the reaction tube as shown in FIGURE. This reaction tube 1 was retained in a molten salt bath 2 at 430° C. In the apparatus illustrated in FIGURE, a raw material fluorene (fluorene concentration 98% by weight) originating in a petroleum process and fed from a feeder 3 via a pipe kept at 140° C. was forwarded to an inlet part of the reaction tube and introduced as mixed with preheated air into a catalyst bed 4. The reaction of fluorene and air was carried out with the feed rate of fluorene fixed at 9.59 mg/minute (as pure fluorene) and the airflow fixed at 500 ml/minute (at 0° C. under one atmosphere). The fluorene concentration in the feed raw material gas at this time was 19.1 g per 1 Nm$^3$ of feed raw material gas.

The gas produced by the reaction was collected via an air-cooled glass collecting tube of 35 mm in inside diameter (not shown) and three aerating vials (not shown) arranged in series and filled with acetone. It was recovered in the form of an acetone solution and then analyzed with a gas chromatography using a column OV-1/0.25 mm ID 50 m (produced by Shimadzu Seisakusho, Ltd. and marketed under product code of "GC-14B"). Consequently, the conversion of fluorene was found to be 99.2 mol %, the selectivity of fluorenone to be 87.4 mol %, and the yield of fluorenone to be 86.8 mol %.

EXAMPLE 1 to 4

The oxidation reaction was carried out by following the procedure of Comparative Example 1 while adjusting the fluorene concentration in the feed raw material gas to 253 g/Nm$^3$ (Example 1), 482 g/Nm$^3$ (Example 2), 901 g/Nm$^3$ (Example 3), and 1031 g/Nm$^3$ (Example 4) by varying the feed rate of fluorene. The results are shown in Table 1.

TABLE 1

|  | Concentration of fluorene (g/Nm$^3$) | Molar ratio of fluorene to molecular oxygen | Spatial velocity of feeding raw material gas (/hr) | Conversion of fluorene (mol %) | Selectivity of fluorenone (mol %) | Yield of fluorenone (mol %) |
| --- | --- | --- | --- | --- | --- | --- |
| Comparative Example 1 | 19.1 | 0.012 | 532 | 99.2 | 87.4 | 86.8 |
| Example 1 | 253 | 0.168 | 549 | 99.1 | 91.7 | 90.9 |
| Example 2 | 482 | 0.328 | 567 | 98.8 | 93.7 | 92.6 |
| Example 3 | 901 | 0.651 | 603 | 98.3 | 95.6 | 94.0 |
| Example 4 | 1031 | 0.759 | 615 | 98.1 | 96.0 | 94.2 |

Concentration of fluorene (g/Nm$^3$) = (Feed rate of fluorene (g/hr))/{(Air flow (Nm$^3$/hr)) + {(Supplied fluorene (g/hr))/(Molecular weight of fluorene)} × 0.0224}
Spatial velocity (/hr) = {(Air flow (Nm$^3$/hr)) + {(Supplied fluorene (g/hr))/(Molecular weight of fluorene)} × 0.0224}/(Volume of catalyst (m$^3$))

Comparative Example 2

In the same apparatus as illustrated in FIGURE, the oxidizing catalyst mentioned above was packed in a bed length of 250 mm on the gas outlet side of the stainless steel reaction tube of 25 mm in inside diameter. This reaction tube was retained in a molten salt bath at 430° C. A raw material fluorene of the tar type having the following composition and supplied from a fluorene raw material feeder via a pipe kept at 140° C. was supplied via the pipe immersed in the molten salt bath so as to be mixed with preheated air and introduced into the catalyst bed.

Composition of raw material (% by weight)

Fluorene (75)

Sulfur (0.2)

9-Methyl fluorene, methyl biphenyl, dibenzofuran, etc. (balance)

The reaction of fluorene and air was carried out with the feed rate of fluorene fixed at 39.3 mg/minute (as pure fluorene) and the air flow fixed at 2050 ml/minute (0° C. under one atmosphere).

The gas produced by the reaction was collected via an air-cooled glass collecting tube of 35 mm in inside diameter, and three aerating vials arranged in series and filled with acetone. It was recovered in the form of an acetone solution and then analyzed with a gas chromatography using a column OV-1/0.25 mm ID/50 m (produced by Shimadzu Seisakusho, Ltd. and marketed under product code of "GC-14B"). Consequently, the conversion of fluorene was found to be 94.2 mol %, the selectivity of fluorenone to be 78.7 mol %, and the yield of fluorenone to be 74.1 mol %.

EXAMPLE 5

The reaction was performed by following the procedure of Comparative Example 2 while using a raw material fluorene originating in the petroleum process containing no sulfur and having the following composition instead. The results are shown in Table 2.

Composition of raw material (% by weight)

Fluorene (96)

Sulfur (0)

Methyl biphenyl, methyl naphthalene, 9-methyl fluorene, etc.

(balance)

EXAMPLE 6

The reaction was performed by following the procedure of Comparative Example 2 while using a raw material fluorene originating in the tar and having the following composition instead. The results are shown in Table 2.

Composition of raw material (% by weight)

Fluorene (94)

Sulfur (0.05)

9-Methyl fluorene, methyl biphenyl, dibenzofuran, etc.

(balance)

EXAMPLE 7

The reaction was performed by following the procedure of Comparative Example 2 while using a raw material fluorene originating in the petroleum process containing no sulfur and having the following composition instead. The results are shown in Table 2.

Composition of raw material (% by weight)

Fluorene (94)

Sulfur (0)

Methyl biphenyl, methyl naphthalene, 9-methyl fluorene, etc.

(balance)

TABLE 2

| | Sulfur content (% by weight) | Conversion of fluorene (mol %) | Selectivity of fluorenone (mol %) | Yield of fluorenone (mol %) |
|---|---|---|---|---|
| Comparative Example 2 | 0.2 | 94.2 | 78.7 | 74.1 |
| Example 5 | 0 | 90.5 | 90.2 | 81.6 |
| Example 6 | 0.05 | 89.7 | 89.1 | 80.0 |
| Example 7 | 0 | 89.4 | 92.1 | 82.3 |

EXAMPLE 8

The reaction was carried out by following the procedure of Example 5 while changing the gas concentration to 460 g/Nm$^3$. The conversion of fluorene was found to be 93.1 mol %, the selectivity of fluorenone to be 95.8 mol %, and the yield of fluorenone to be 89.2 mol %. The highest temperature of the catalyst bed was 480° C.

Comparative Example 3

The reaction was carried out by following the procedure of Example 8 while using the raw material fluorene used in Comparative Example 2 instead. The highest temperature of the catalyst bed surpassed 560° C. Since the temperature still continued to rise, the reaction was terminated.

The preferred embodiments described herein are therefore illustrative and not restrictive, the scope of the invention being indicated by the appended claims and all version which come within the meaning of the claims are intended to be embraced therein.

The entire disclosure of Japanese Patent Application Nos. 7-321,370 and 7-321,371 both filed on Dec. 11, 1995 including specifications, claims, drawing and summaries are incorporated herein by reference in its entirely.

What is claimed is:

1. A method for the production of fluorenone by the vapor-phase catalytic oxidation of fluorene with a molecular oxygen-containing gas, which comprises:

adjusting the molar ratio of fluorene to molecular oxygen in a feed raw material gas containing fluorene as a raw material and a molecular oxygen-containing gas in the range of 1:1 to 0.13:1 and the fluorene contents per 1 Nm$^3$ of the feed raw material gas being in the range of not less than 200 g/Nm$^3$; and subjecting the oxidation of fluorene in the presence of a catalyst formed of at least one metal element of the fifth and sixth groups of the periodic table.

2. A method according to claim 1, wherein said molecular oxygen-containing gas is air.

3. A method according to claim 1, wherein said catalyst further contains titania, and an alkali metal compound.

4. A method according to claim 3, wherein an atomic ratio of said alkali metal to vanadium is in the range of 0.8:1 to 8:1.

5. A method for the production of fluorenone by the vapor-phase catalytic oxidation of fluorene with a molecular oxygen-containing gas, which comprising:

preparing the raw material fluorene having a sulfur content at or below 0.15% by weight; and subjecting the oxidation in the presence of a catalyst formed of at least one metal element of the fifth and sixth groups of the periodic table.

6. A method according to claim 5, wherein a molar ratio of fluorene to molecular oxygen containing fluorene as a raw material gand a molecular oxygen-containing gas is in the range of 1:1 to 0.13:1.

7. A method according to claim 5, wherein said molecular oxygen-containing gas is air.

8. A method according to claim 5, wherein said catalyst further contains titania, and an alkali metal compound.

9. A method according to claim 8, wherein an atomic ratio of said alkali metal to vanadium is in the range of 0.8:1 to 8:1.

10. A method according to claim 1, wherein the fluorene content is in the range of 200–1280 g/Nm$^3$.

11. A method according to claim 1, wherein the fluorene content is in the range of 450–1170 g/Nm$^3$.

12. A method according to claim 1, wherein the fluorene content is in the range of 900–1060 g/Nm$^3$.

13. A method according to claim 1, wherein the molar ratio of fluorene to molecular oxygen is in the range of 0.9:1 to 0.3:1.

14. A method according to claim 1, wherein the molar ratio of fluorene to molecular oxygen is in the range of 0.8:1 to 0.6:1.

* * * * *